United States Patent
Nesterenko et al.

(10) Patent No.: US 10,851,028 B2
(45) Date of Patent: *Dec. 1, 2020

(54) PROCESS FOR DEHYDRATION OF MONO-ALCOHOL(S) USING A MODIFIED CRYSTALLINE ALUMINOSILICATE

(71) Applicants: TOTAL RESEARCH & TECHNOLOGY FELUY, Seneffe (BE); IFP ENERGIES NOUVELLES, Rueil Malmaison (FR)

(72) Inventors: Nikolai Nesterenko, Nivelles (BE); Colin Dupont, Brussels (BE); Vincent Coupard, Villeurbanne (FR); Sylvie Maury, Saint Maurice d'Argoire (FR); Thibault Heinz, Solaize (FR)

(73) Assignees: TOTAL RESEARCH & TECHNOLOGY FELUY, Seneffe (BE); IFP ENERGIES NOUVELLES, Rueil Malmaison (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/330,784

(22) PCT Filed: Sep. 6, 2017

(86) PCT No.: PCT/EP2017/072294
§ 371 (c)(1),
(2) Date: Mar. 6, 2019

(87) PCT Pub. No.: WO2018/046515
PCT Pub. Date: Mar. 15, 2018

(65) Prior Publication Data
US 2019/0233348 A1    Aug. 1, 2019

(30) Foreign Application Priority Data

Sep. 9, 2016  (EP) .................... 16290172

(51) Int. Cl.
| | | |
|---|---|---|
| *C07C 1/24* | (2006.01) | |
| *B01J 37/10* | (2006.01) | |
| *B01J 29/65* | (2006.01) | |
| *C01B 39/02* | (2006.01) | |
| *B01J 21/08* | (2006.01) | |
| *B01J 35/02* | (2006.01) | |
| *B01J 37/00* | (2006.01) | |
| *C07C 5/27* | (2006.01) | |
| *B01J 29/70* | (2006.01) | |

(Continued)

(52) U.S. Cl.
CPC ............. *C07C 1/24* (2013.01); *B01J 21/08* (2013.01); *B01J 29/65* (2013.01); *B01J 29/70* (2013.01); *B01J 29/7023* (2013.01); *B01J 29/7026* (2013.01); *B01J 29/7038* (2013.01); *B01J 29/7042* (2013.01); *B01J 29/7046* (2013.01); *B01J 35/023* (2013.01); *B01J 37/0009* (2013.01); *B01J 37/0063* (2013.01); *C01B 39/026* (2013.01); *C07C 5/2775* (2013.01); *B01J 2029/081* (2013.01); *B01J 2229/16* (2013.01); *B01J 2229/34* (2013.01); *B01J 2229/36* (2013.01); *B01J 2229/40* (2013.01); *B01J 2229/42* (2013.01); *C07C 11/09* (2013.01); *C07C 2529/65* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 4,282,389 A |  | 8/1981 | Droste et al. |
| 4,621,161 A | * | 11/1986 | Shihabi ............... B01J 29/40 585/408 |
| 5,523,510 A |  | 6/1996 | Pellet et al. |
| 9,233,886 B2 | * | 1/2016 | Adam .................. B01J 29/85 |
| 2016/0074845 A1 | * | 3/2016 | Detjen ................. B01J 37/08 585/321 |

FOREIGN PATENT DOCUMENTS

| | | |
|---|---|---|
| EP | 0034444 A2 | 8/1981 |
| EP | 0134333 A1 | 3/1985 |
| EP | 2348005 A1 | 7/2011 |
| WO | 2011/089235 A1 | 7/2011 |
| WO | 2011/113834 A1 | 9/2011 |
| WO | 2013/014081 A1 | 1/2013 |

OTHER PUBLICATIONS

International Search Report issued in Application No. PCT/EP2017/072294, dated Dec. 12, 2017, 4 pages.

(Continued)

*Primary Examiner* — Philip Y Louie
(74) *Attorney, Agent, or Firm* — Albert Shung

(57) ABSTRACT

The invention relates to a process for dehydration of a mono-alcohol, or of a mixture of at least two mono-alcohols, having at least 2 carbon atoms and at most 7 carbon atoms into olefins having the same number of carbons, wherein the process uses a catalyst composition that comprises a modified crystalline aluminosilicate has an acidity between 350 and 500 µmol/g that comprises, and further wherein the catalyst composition is obtained by a process comprising the steps of providing a crystalline aluminosilicate having a Si/Al framework molar ratio greater than 10; and steaming said crystalline aluminosilicate, or said shaped and/or calcined crystalline aluminosilicate at a temperature ranging from 100° C. to 380° C.; and under a gas phase atmosphere, without liquid, containing from 5 wt % to 100 wt % of steam; at a pressure ranging from 2 to 200 bars; at a partial pressure of $H_2O$ from 2 bars to 200 bars; and said steaming being performed during at least 30 min and up to 144 h.

15 Claims, No Drawings

(51) Int. Cl.
   *B01J 29/08*    (2006.01)
   *C07C 11/09*    (2006.01)

(56) References Cited

OTHER PUBLICATIONS

Gon Seo et al, "The role of carbonaceous deposits in the skeletal isomerization of 1-butene over ferrierite zeolites", Catalysis Letters, (1996), vol. 41, No. 3-4, pp. 189-194.
D. Rutenbeck et al, "Investigations on the reaction mechanism of the skeletal isomerization of n-butenes to isobutene", Applied Catalysis A: General, (Feb. 2001), vol. 208, No. 1-2, pp. 153-161.
Xu W-Q et al, "Modification of Non-Template Synthesized Ferrierite/Zsm-35 for N-Butene Skeletal Isomerization to Isobutylene", Journal of Catalysis, Academic Press, Duluth, MN, US, (1996), vol. 163, pp. 232-244.
Dazhi Zhang et al, "n-Butanol to iso-butene in one-step over zeolite catalysts", Applied Catalysis A: General, Elsevier Science, Amsterdam, NL, vol. 403, No. 1, (May 28. 2011), pp. 1-11.

\* cited by examiner

PROCESS FOR DEHYDRATION OF MONO-ALCOHOL(S) USING A MODIFIED CRYSTALLINE ALUMINOSILICATE

CROSS-REFERENCE TO RELATED APPLICATIONS

This application claims the benefit of PCT/EP2017/072294 filed Sep. 6, 2017, which claims priority from EP 16290172.2 filed Sep. 9, 2016, which are incorporated herein by reference in their entireties for all purposes.

TECHNICAL FIELD

The present invention relates generally to the field of dehydration and skeletal isomerization of alcohols on acidic catalysts to make corresponding olefins, preferably of alcohols having at least four carbon atoms for the production of olefins having the same number of carbon atoms as the alcohols. The present invention relates to a catalyst composition comprising a modified crystalline aluminosilicate preferably of the group FER (Framework Type FER) or SZR and to a process for the preparation thereof. The present invention also relates to the use of said catalyst composition in a dehydration process of alcohols and to the use of the olefins so-produced in various subsequent processes.

BACKGROUND OF THE INVENTION

The dehydration reactions of alcohols to produce alkenes have been known for a long time. Solid acid catalysts are widely used for alcohol dehydration and the conversion of alcohols therewith is nearly complete. However, in view of the potential downstream applications of olefins, it is of particular importance to limit the amount of secondary products and ensure a stable catalyst performance to gain in process efficiency and to save expensive steps of downstream separation/purification as well as to recover the catalyst activity by regeneration. Zeolites-based catalysts are particularly interesting for alcohols dehydration due to their high-activity, high-yield of corresponding olefins, and a possibility to operate under high-pressure conditions, which offers the best energy efficiency solutions for the technology.

Dehydration of ethanol on zeolites was described in WO2011/089235. The process for the dehydration of ethanol to ethylene was carried out in presence of zeolite catalysts and provides an alternative route to ethylene from biobased products if ethanol is obtained by fermentation of carbohydrates.

Dehydration of isobutanol to the corresponding olefins brings a perspective route to produce the renewable feedstock for petrochemicals and refining applications. Unfortunately, the direct conversion of isobutanol over a conventional dehydration catalyst, for example on alumina, leads to a product rich in isobutene. Selective production of linear butenes from iBuOH requires again a zeolite-based catalyst. The cut that is rich in linear butenes is often interesting as feedstock for metathesis, sulfuric acid catalyzed alkylation, oligomerization, oxidative dehydrogenation to butadiene, for the use as a copolymer. Therefore, the efficient catalyst for one-pot process converting isobutanol to the effluent rich in the linear butenes is sought.

While many skeletal isomerization catalysts for the conversion of n-butenes into isobutene have been developed, the reverse skeletal isomerization of isobutene into n-butenes has been rarely mentioned. Among the catalysts being active and selective, there are mostly unidirectional 10-membered ring zeolites. WO2011/113834 relates to the simultaneous dehydration and skeletal isomerization of isobutanol on acid catalysts. The process discloses the contact of a stream comprising isobutanol with a catalyst able to make such reaction. The catalyst was a crystalline silicate, a dealuminated crystalline silicate, or phosphorus modified crystalline silicate having Si/Al higher than 10; or silicoaluminaphosphate molecular sieve, or a silicated, zirconated or titanated or fluorinated alumina. The conversion of isobutanol was almost complete with selectivity in butenes ranging from 95 wt % to 98 wt %. The selectivity in isobutene was around 41-43%. This document indicates that steaming at temperatures above 400° C. leads to a modification of the acidity of the catalyst and to the removal of aluminium from the crystalline silicate framework. Subsequently, it is necessary to treat the catalyst via a leaching to remove the aluminium and to increase the ratio Si/Al. The steps of steaming and leaching are associated in this document.

However, crystalline silicate catalysts deactivate fast and have limited regenerability. Hence, there is still a need for selective catalysts towards linear olefins and having improved regenerability.

In catalysis letters 41 (1996) 189-194, Gon Seo et al. studied the impact of coke deposits on ferrierite zeolites for the reaction of skeletal isomerization of 1-butene. The ferrierite studied was calcined at 500° C. for 16 h without any other particular treatment aiming at modifying its acidity. This ferrierite has a Si/Al ratio of 21 and it is further covered with coke using a plasma deposition before the reaction of skeletal isomerization of 1-butene is studied.

In WO2013/014081, SUZ-4 is studied for the methanol to olefin reaction. This document discloses the possibility of steaming the catalyst at a temperature of at least 400° C. followed by a leaching, i.e. a washing, of the steamed solid with an aqueous acid solution. Such treatment is said to increase the Si/Al ratio.

In Applied Catalysis A: General 208 (2001) 153-161, Rutenbeck et al. studied the skeletal isomerization of n-butenes to isobutene. The catalyst studied was a ferrierite having a Si/Al ratio in the range of 20-70. A treatment of the ferrierite with the inorganic acid HCl was performed to obtain the protonic form of the ferrierite.

In the Journal of Catalysis 163, 232-244 (1996), Wen-Qing Xu et al. studied the modification ferrierite for the skeletal isomerization of n-butene. The ferrrierite used presents a Si/Al ratio of 8.8. Treatment of the ferrierite also includes steaming at a temperature of at least 550° C. and acidic treatment with HCl or $HNO_3$.

In EP2348005, the use of a ferrierite based catalyst for the dehydration of isobutanol is described. It is disclosed that the ferrierite may be used directly without further treatment or that it may be used once being steamed and dealuminated with an acidic treatment.

In Applied Catalysis A: General 403 (2011) 1-11, Dazhi Zhang et al. is described the use of a ferrierite for the conversion of n-butanol to iso-butene. Such ferrierite was calcined at 550° C. but did not undergo any further treatment.

In U.S. Pat. No. 5,523,510, the use of an acid wash ferrierite based catalyst for the skeletal isomerization of n-olefins to iso-olefins is described. Such acid wash is performed with HCl. In all the examples, the ferrierite is firstly steamed above 400° C. at atmospheric pressure before being acid washed.

In EP 0 134 333, a method of preparation of a cracking catalyst comprising a zeolite with a Si/Al ratio of at least 250 with a binder is described.

In EP 0 034 444, a method for increasing the catalytic of acid zeolite catalyst is described.

To summarize, zeolite-based catalysts are important for alcohols dehydration, skeletal isomerization of butenes, MTO and many other reactions. To tune the Si/Al ratio of zeolite, dealumination via steaming at a temperature above 400° C. under atmospheric pressure followed by a leaching is usually performed. However, such treatment leads to the formation of extra framework aluminium and partial destruction of the zeolite framework that induce different diffusion properties. Consequently, the selectivity of a catalyst prepared with a steamed and leached zeolite is generally impacted by the steaming. In the particular case of FER and SZR (SUZ-4), steaming followed by leaching has an even stronger impact on the selectivity due to the plate-shaped crystal morphology of those frameworks. However, FER and SZR are interesting because of their very high selectivity. Additionally, those structure types are particularly difficult to synthesize with a Si/Al atomic ratio above 35. Tuning of the acidity is consequently not easy albeit necessary. The present invention aims at providing catalyst compositions that address the above-discussed drawbacks of the prior art and solve the problem.

SUMMARY OF THE INVENTION

In particular, it is an object of the present invention to provide a process for dehydration of a mono-alcohol, or of a mixture of at least two mono-alcohols using a catalyst based on modified crystalline aluminosilicate or zeolite (both terms are equivalent) being preferably of the Framework Type FER or SZR and having a Si/Al framework molar ratio greater than 10 exhibiting substantially complete once-through conversion of the C2-C7 alcohols to the corresponding olefins.

In a preferred mode, the present invention provides a catalyst showing good to excellent selectivity to linear olefins, above thermodynamic equilibrium, in simultaneous dehydration and skeletal isomerization reaction of alcohols having at least four carbon atoms.

In one aspect of the present invention, a process for modifying a crystalline aluminosilicate is provided as well as a modified crystalline aluminosilicate obtained by said process. Said modified crystalline aluminosilicate is for instance useful for the preparation of a catalyst that can be used in the conversion of the C2-C7 alcohols to the corresponding olefins. In a preferred mode said modified crystalline aluminosilicate is particularly useful for the simultaneous dehydration and skeletal isomerization of a mono-alcohol having at least four carbon atoms into olefins having the same number of carbons. In a most preferred application, said mono-alcohol is isobutanol, i.e. 2 methyl propan-1-ol.

According to a first aspect, the invention provides a process for dehydration of a mono-alcohol, or of a mixture of at least two mono-alcohols, having at least 2 carbon atoms and at most 7 carbon atoms into olefins having the same number of carbons, the process comprising the following steps:
  i.) providing a catalyst composition;
  ii.) providing a feed (A) comprising said mono-alcohol, or said mixture of at least two mono-alcohols, optionally water, optionally an inert component;
  iii.) contacting said feed (A) with said catalyst at conditions effective to dehydrate at least a portion of said mono-alcohol;
  iv.) recovering an effluent (B) and removing water, the inert component if any and unconverted alcohols if any to get said olefins having the same number of carbons as said mono-alcohol the process being remarkable in that said catalyst composition comprises a modified crystalline aluminosilicate has an acidity between 350 and 500 µmol/g measured by temperature programmed desorption of ammonia, wherein catalyst composition is obtained by a process comprising the following steps:
  a) providing a crystalline aluminosilicate having a Si/Al framework molar ratio greater than 10;
  b) optionally shaping and/or calcining said crystalline aluminosilicate;
  c) steaming said crystalline aluminosilicate, or said shaped and/or calcined crystalline aluminosilicate:
    at a temperature ranging from 100° C. to 380° C.; and
    under a gas phase atmosphere, without liquid, containing from 5 wt % to 100 wt % of steam the rest being one or more gas selected from $N_2$, $CO_2$, Ar, He, $CH_4$, air, or any mixture of thereof; with preference air is selected from air and depleted air containing below 10 wt % of oxygen as based on the total weight of the depleted air, preferably below 5 wt %, more preferably below 1 wt %; and
    at a pressure ranging from 2 to 200 bars; and
    at a partial pressure of $H_2O$ from 2 bars to 200 bars; and said steaming being performed during at least 30 min and up to 144 h.

The content of steam in wt % is based on the total weight of the gas phase atmosphere.

The process for modifying a crystalline aluminosilicate avoids the formation of the defects in the crystalline aluminosilicate, it avoids blocking the porosity simultaneously to a decrease of the effective number of the acid sites. Indeed, it has been discovered that a mild steaming, i.e. steaming performed at a maximum temperature of 380° C. and under pressure, i.e. a pressure higher than the atmospheric pressure is particularly beneficial for the activity, selectivity and regenerability of the catalyst prepared with said modified crystalline aluminosilicate. It has been particularly discovered that modified crystalline aluminosilicate being prepared according to the above-mentioned recipe presents acidic properties that are particularly suitable for the dehydration of mono-alcohol or of mixture of alcohols having 2 to 7 carbon atoms as well as for the simultaneous dehydration and skeletal isomerization of a mono-alcohol(s) into olefins having the same number of carbons. Such modified crystalline aluminosilicate has a sufficient acidity to perform the dehydration reaction with a good activity while not being too acidic thereby maintaining a suitable selectivity toward normal olefins. Said modified crystalline aluminosilicate is therefore particularly useful for instance in the preparation of a catalyst that can be used for alcohol dehydration into corresponding olefins having the same number of carbons said mono-alcohol being preferably ethanol, isobutanol, i.e. 2 methyl propan-1-ol.

With preference, one or more of the following features can be used to better define the inventive process for modifying a crystalline aluminosilicate:
  The step c) of steaming said crystalline aluminosilicate is performed at a temperature of at least 200° C., preferably at least 250° C.

The step c) of steaming said crystalline aluminosilicate is performed a temperature of at most 350° C.

The step c) of steaming said crystalline aluminosilicate is performed at a pressure ranging from 2 to 20 bars, more preferably ranging from 2 to 15 bars.

The step c) of steaming said crystalline aluminosilicate is performed at a partial pressure of $H_2O$ from 3 to 10 bars.

No any leaching treatment is performed either before step a) or after step c) in order to maintain constant the concentration of aluminium in the modified crystalline aluminosilicate;

A step of washing or ion exchange with for instance an alkali metal or $NH_4$ salts is performed after step c) or before step b).

A calcination step of the product obtained after step c) or before step b) is performed.

An step of recovering said modified crystalline aluminosilicate is performed after c) or after any of the other optional steps.

The modified crystalline aluminosilicate is a 10 membered ring zeolite preferably of the Framework Type FER, MWW, EUO, MFS, ZSM-48, MTT, MFI, MEL, TON or SZR and is preferably chosen among ferrierite, FU-9, ISI-6, NU-23, Sr-D, ZSM-35, ZSM-57 or SUZ-4 or any mixture thereof.

The modified crystalline aluminosilicate has Si/Al framework molar ratio ranging from 10 to 100, preferably ranging from 10 to 65, more preferably from 20 to 50, more preferably ranging from 21 to 30.

The modified crystalline aluminosilicate has a content in transition metals or cations thereof lower than 1000 ppmwt, preferably measured by the method ASTM UOP961-12, said transition metals belonging to any of the columns 3 to 12 of the Periodic Table. Indeed, transition metals or cations thereof are particularly detrimental for the catalyst selectivity because they catalyze the formation of heavy hydrocarbons.

The modified crystalline aluminosilicate obtained by said process for modifying a crystalline aluminosilicate has an acidity between 350 and 525 µmol/g preferably between 400 and 500 µmol/g measured by temperature programmed desorption of ammonia.

The process for modifying a crystalline aluminosilicate is remarkable in that said crystalline aluminosilicate is shaped (µ-spheres by spray-drying or droplet, tablets, extrudates: trilobes, quadrilobes, cylinders) preferably in quadrilobes extrudates prior to any of steps a) to c) with a binder being preferably a silicic binder, $AlPO_4$, clay, a zirconia, or a titania oxide more preferably being silica, $SiO_2$, i.e. said binder contains at least 99.5% of $SiO_2$ with a maximum concentration of aluminium, gallium, boron, iron and/or chromium of 1000 ppm wt, preferably 500 ppm wt, more preferably 200 ppm wt.

Said crystalline aluminosilicate is shaped or extruded prior to any of steps a) to c) with a binder selected from $AlPO_4$, clay, zirconia, titania oxide or silica, more preferably the binder comprises or is silica.

The process for modifying a crystalline aluminosilicate is remarkable in that preferably after step c) a further step of shaping or extruded preferably in quadrilobes is performed with a binder being preferably a silicic binder, $AlPO_4$, clay, a zirconia, or a titania oxide more preferably being silica, $SiO_2$, i.e. said binder contains at least 99.5% of $SiO_2$ with a maximum concentration of aluminium, gallium, boron, iron and/or chromium of 1000 ppm wt, preferably 500 ppm wt, more preferably 200 ppm wt.

The product obtained after step c) is further shaped or extruded with a binder selected from $AlPO_4$, clay, zirconia, titania oxide or silica, preferably the binder comprises or is silica.

The binder is selected to comprise at least 85 wt % of silica as based on the total weight of the binder, preferably at least 99.5 wt %.

The binder is selected to comprise less than 1000 ppm by weight as based on the total weight of the binder of aluminium, gallium, boron, iron and/or chromium, preferably less than 500 wt ppm, more preferably less than 200 wt ppm.

Said steaming of step c) is performed on a shaped or extruded crystalline aluminosilicate in situ prior to step iii.) of said process for dehydration of a mono-alcohol to obtain said catalyst.

The process for modifying a crystalline aluminosilicate is further remarkable in that preferably neither any steaming at a temperature higher than 380° C. nor any leaching has been performed on said crystalline aluminosilicate prior to being used for instance in the dehydration of a mono-alcohol into olefins having the same number of carbons.

The process for modifying a crystalline aluminosilicate is further remarkable in that it is a versatile process: it can be performed in situ or ex situ. Said process for modifying a crystalline aluminosilicate can preferably be performed on a catalyst comprising the crystalline aluminosilicate to be modified. Said process for modifying a crystalline aluminosilicate can more preferably be performed on a catalyst comprising the crystalline aluminosilicate to be modified already loaded and prior to its use for instance in a process for dehydration of a mono-alcohol. Alternatively said process for modifying a crystalline aluminosilicate can be performed on the crystalline aluminosilicate to be modified prior to its incorporation and/or prior to the shaping into a catalyst.

The process for dehydrating a mono-alcohol, or of a mixture of at least two mono-alcohols, is further remarkable in that said conditions effective to the simultaneous dehydration and skeletal isomerization of a mono-alcohol into olefins having the same number of carbons are any combinations of:

Adiabatic or isotherm operating conditions or any of intermediate conditions in between the adiabatic and the isotherm including for instance partial heat compensation or intermediate re heating; and/or An inlet temperature ranging from 200° C. to 500° C., preferably 225° C. to 450° C., most preferably 250° C. to 400° C.; and/or A pressure ranging from 0.5 bar to 15 bars absolute (50 kPa to 1.5 MPa) preferably 0.5 bar to 10 bars absolute (50 kPa to 1.0 MPa) most preferably 1.2 to 9 bars absolute (0.12 MPa to 0.9 MPa); and/or A Weight Hourly Space Velocity (WHSV) ranging from 1 to 30 $h^{-1}$ preferably from 2 to 21 $h^{-1}$, more preferably from 3 to 9 $h^{-1}$, wherein the WHSV represents the weight flow rate of said mono-alcohol at the inlet of the reactor divided by the mass of the catalyst in said reactor; and/or Said feed (A) having a partial pressure of alcohols from 0.1 to 15 bars absolute (0.01 MPa to 1.5 MPa) more preferably from 0.5 to 9 bars absolute (0.05 MPa to 0.9 MPa).

the process for dehydrating a mono-alcohol is further remarkable in that said mono-alcohol(s) has at least four carbon atoms and at most five carbon atoms and in that said dehydration of a mono-alcohol is performed together with a skeletal isomerization the process for dehydrating a mono-alcohol is further remarkable in that said mono-alcohol is isobutanol, i.e. 2 methyl propan-1-ol that is converted into n-butenes and isobutene It has been discovered that said modified aluminosilicate are particularly suitable for the dehydration of alcohols. In particular, the above described ranges of acidity are perfectly well suited for having a sufficient catalyst activity while maintaining the selectivity at a sufficient level.

The process for modifying a crystalline aluminosilicate is particularly versatile. The steaming can be applied directly after the synthesis of the crystalline aluminosilicate or it can be applied once the catalyst has been shaped or extruded with a binder. Said process for modifying a crystalline aluminosilicate can also be performed in situ, i.e. once the catalyst comprising a crystalline aluminosilicate is loaded in a dehydration reactor or in the dehydration and skeletal isomerization reactor, i.e. prior to its use. In this latter case there is no need to have a dedicated unit to perform the steaming under pressure. Catalyst manufacturers do not necessarily have the facilities to perform a steaming under pressure, but it is still possible to prepare said modified crystalline aluminosilicate in situ of the dehydration and optionally isomerization unit.

Additionally, it has been discovered that the process for modifying an aluminosilicate leads to improved properties. Without willing to be bound by any theory, it is assumed that a low temperature steaming associated with an increase partial pressure during the steaming and the absence of any leaching is particular beneficial for the activity and selectivity of the modified crystalline aluminosilicate. Therefore to maintain the good activity and selectivity, any further steaming at a high temperature or any further leaching should be avoided.

DETAILED DESCRIPTION OF THE INVENTION

The terms "catalyst" and "catalyst composition" are used interchangeably and refer to a composition comprising a crystalline aluminosilicate and a binder. According to the invention, the catalyst composition comprising a modified crystalline aluminosilicate comprises a binder, preferably an inorganic binder. The catalyst composition comprises from 5 to 95 wt % as based on the total weight of the catalyst of crystalline aluminosilicate, preferably from 10 to 90 wt %, more preferably at least 20 to 80 wt % even more preferably from 30 to 70 wt %.

In a preferred embodiment, the crystalline aluminosilicate or the modified crystalline aluminosilicate of the Framework Type FER is a crystalline aluminosilicate containing advantageously at least one 10-membered ring into the structure based on T-atoms, i.e. on the Al and Si atoms contained in said ring. The family of Framework Type FER includes Ferrierite, [B—Si—O]-FER, [Ga—Si—O]-FER, [Si—O]-FER, [Si—O]-FER, FU-9, ISI-6, Monoclinic ferrierite, NU-23, Sr-D, ZSM-35, and SUZ-4. Preferably, the modified crystalline aluminosilicate of the Framework Type FER is Ferrierite. The process for modifying a crystalline aluminosilicate does not change the Framework Type FER.

The Si/Al framework molar ratio of the modified crystalline aluminosilicate may be at least 11, preferably at least 15, more preferably at least 20, even more preferably at least 21, most preferably at least 22, and even most preferably at least 25. Preferably, the Si/Al framework molar ratio of the modified crystalline aluminosilicate may be at most 150, preferably at most 100, more preferably at most 75, even more preferably at most 65, most preferably at most 55 and even most preferably at most 35. In a preferred embodiment, the Si/Al framework molar ratio of the modified crystalline aluminosilicate may range from 11 to 150, preferably from 15 to 100, more preferably from 20 to 100, even more preferably from 20 to 75, and in particular from 25 to 35. In a preferred embodiment, the Si/Al framework molar ratio of the modified crystalline aluminosilicate is ranging from 10 to 65. Advantageously the modified crystalline aluminosilicate shows a high crystallinity of its zeolite phase, said crystallinity being similar to the crystallinity of the parent zeolite before modification, i.e. said crystallinity is similar to the crystallinity of the crystalline aluminosilicate before being modified. A similar crystallinity is evidenced via the X ray diffraction patterns (less than 20% of difference measured on the area below the X ray curves), i.e. the X ray diffraction pattern of the crystalline aluminosilicate (before being modified) is the same as the crystallinity of the modified crystalline aluminosilicate.

In a preferred embodiment, said modified crystalline aluminosilicate has content in redox transition metals or cations thereof lower than 1000 ppm wt, said transition metals belonging to one of the columns 3 to 12 of the Periodic Table. Preferably, said metals are Fe, Co, Ni, Cu, Mo, Mn, Ti, Zn, V, Cr, Ru, Rh, Cd, Pt, Pd, Au, Zr. Preferably, said modified crystalline aluminosilicate has content in metals or cations thereof as defined above lower than 500 ppm wt, more preferably lower than 200 ppm wt, most preferably lower than 100 ppm wt, in particular lower than 50 ppm wt being for instance measured by the method ASTM UOP961-12.

In another specific embodiment, the catalyst comprising a modified crystalline aluminosilicate may comprise a binder, preferably an inorganic binder. The binder is selected so as to be resistant to the temperature and other conditions employed in the dehydration process of the invention. The binder is an inorganic material selected from clays, silica, metal silicate, metal oxides (such as $ZrO_2$), aluminophosphate binders, in particularly, stoichiometric amorphous aluminophosphate or gels including mixtures of silica and metal oxides. It is desirable to provide a catalyst having good crush strength. This is because, in commercial use, it is desirable to prevent the catalyst from breaking down into powder-like materials. Such clay or oxide binders have been employed normally only for the purpose of improving the crush strength of the catalyst. Preferably, said binder is selected from the group consisting of clays, silica, titania, aluminophosphate, titania-silica. A particularly preferred binder for the catalyst composition of the present invention is silica. The relative proportions of the finely divided modified crystalline aluminosilicate material and the inorganic oxide matrix of the binder can vary widely. Typically, the binder content may range from 5 to 95% by weight, more typically from 20 to 85% by weight, based on the weight of the catalyst composition. By adding a binder to the catalyst composition, this latter may be formulated into pellets, extruded into other shapes, or formed into spheres or a spray-dried powder. The binder is preferably selected to comprise at least 85 wt % of silica as based on the total weight of the binder, preferably at least 90 wt %, more preferably at least 95 wt % even more preferably at least 99 wt % and most preferably at least 99.5 wt %. The binder is preferably selected to comprise less than 1000 ppm by weight as based on the total weight of the binder of aluminium, gallium, boron, iron and/or chromium, preferably less than 500 wt ppm, more preferably less than 200 wt ppm.

The modified crystalline aluminosilicate may be in H-form. The H-form of a modified crystalline aluminosilicate of the Framework Type FER means that it comprises oxygen atoms bonded to one aluminium atom and one silicon atom, and which is protonated with a hydrogen atom, resulting in the following sequence —[—Al—O(H)—Si—]—. In the present invention, the modified crystalline aluminosilicate may be essentially under H-form, which means containing less than 1000 ppmwt of the total amount of the alkali ions and the alkaline earth ions. In another embodiment, the modified crystalline aluminosilicate is partly under H-form. It means that in said modified crystalline aluminosilicate part of the hydrogen atoms bonded to oxygen atoms in the following sequence —[—Al—O(H)—Si—]— is substituted by metallic ions, preferably alkali ions, alkaline earth ions or silver ions. Preferably, the alkali ions or alkaline earth ions may be Na, K, Cs, Li, Mg or Ca being measured via chemical analysis with for instance the method ASTM UOP961-12.

Said process for modifying a crystalline aluminosilicate is particularly remarkable in that, preferably, no leaching is performed. The term leaching shall encompass any treatment of a solid with an acidic medium (inorganic or organic) or complexing agent able to remove aluminium from the crystalline aluminosilicate framework or preferably extra framework aluminium (EFAL).

As non-limiting example, said acidic medium and/or said complexing agent used in leaching treatment shall encompass citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyl ethylene diamine triacetic acid, ethylene diamine tetraacetic acid, trichloroacetic acid, trifluoroacetic acid, methansulfonic or a salt of such an acid (e.g. the sodium salt) or a mixture of two or more of such acids or salts. Inorganic acids, such as nitric acids or halogenic acids, are also encompassed in the meaning of acidic medium. Complexing agent shall encompass any organic molecule able to form a complex with aluminium and preferably forms a water-soluble complex with aluminium in order to remove aluminium and preferably extra framework aluminium (EFAL). A particularly preferred complexing agent may comprise an amine, preferably ethylene diamine tetraacetic acid (EDTA) or a salt thereof, in particular the sodium salt thereof. The term complexing agent shall encompass also organic acidic medium but not only. The person skilled in the art can recognize the organic medium able to remove the aluminium or EFAL from a crystalline aluminosilicate. As a guidance, it may be put forward that said organic medium refers to organic molecules able to form a complex with aluminium and preferably forms a water-soluble complex with aluminium in order to remove aluminium or EFAL, i.e. in order to remove at least 5 wt % preferably 10 wt % of the aluminium or EFAL present on the crystalline aluminosilicate. It shall also be clear that said modified crystalline aluminosilicate is not preferably further leached prior to its use for instance in the process for dehydrating mono-alcohols.

In an optional embodiment, the process for modifying a crystalline aluminosilicate encompasses an optional calcinations. Said calcinations are performed to burn organic component that may be present on the crystalline aluminosilicate but under conditions avoiding the formation of pentahedral aluminium. In particular, at the inlet of the calcinations reactor, the calcination gas should contain less than 1000 ppmwt of water. Therefore, even if the crystalline aluminosilicate contains interstitial water, the presence of water inside the calcinations reactor is low enough to avoid a partial steaming of the crystalline aluminosilicate. During the optional calcinations, the crystalline aluminosilicate may be under the $NH_4$ form, the Na, K or H-forms. The calcinations can be performed under atmospheric pressure or alternatively at a pressure up to 9 bars. The calcination gas may contain inert components such as for instance $N_2$, Ar, He, $CO_2$, or other species such as for instance natural gas components or CO, $N_2O$ which are not inert under the calcination conditions but do not lead to the deposition of any molecules such as coke on the crystalline aluminosilicate. The calcinations may be alternatively be performed under depleted air or the calcination gas may contains below 10 wt % of oxygen or preferably below 5 wt % or even below 1 wt % of oxygen, as based on the total weight of the depleted air, in order to avoid the thermal runaway when organic molecules are burnt during calcinations. Indeed, in depleted air the content of oxygen is based on the total weight of said depleted air. The optional calcinations can be performed at a temperature not higher than 600° C., preferably 550° C., most preferably 500° C., and with a temperature increase of less than 10° C./min, preferably less than 1° C./min, the most preferably at 0.5° C./min, for a period of at least 30 min, preferably at least 2 h and at most 48 h and under a gas flow containing at most 1000 ppm volume of water measured at the inlet of the calcination reactor. The optional calcinations can either be performed in situ or ex situ, i.e. calcinations can be applied directly after the synthesis of the crystalline aluminosilicate or after the process for modifying the crystalline aluminosilicate or it can be applied once the catalyst has been shaped or extruded with a binder. Said optional calcinations can also be performed in situ, i.e. once the catalyst comprising a crystalline aluminosilicate or a modified crystalline aluminosilicate is loaded in a dehydration reactor or in the dehydration and skeletal isomerization reactor, i.e. prior to its use in a process for dehydrating.

Preferably, the mono-alcohol or the mixture of at least two mono-alcohols have at least four carbon atoms and at most five carbon atoms. Said mono-alcohol is preferentially a primary mono-alcohol substituted by an alkyl group in position 2. Preferably, the mono-alcohols are provided from biomass fermentation or biomass gasification to syngas followed by a modified Fischer-Tropsch synthesis.

Preferably, the alcohol(s) may be 1-butanol, 2-butanol, isobutanol, pentan-1-ol, 3-Methylbutan-1-ol, 2-Methylbutan-1-ol, 2,2-Dimethylpropan-1-ol, pentan-3-ol, Pentan-2-ol, 3-Methylbutan-2-ol, 2-Methylbutan-2-ol, or mixture thereof with the proviso that the mixture contains alcohols having the same number of carbon atoms or optionally presenting a different number of carbon atoms. For example, a mixture of butanol comprises two or more of the following alcohols: 1-butanol, 2-butanol, isobutanol. A mixture of pentanol comprises two or more of the following alcohols: pentan-1-ol, 3-methylbutan-1-ol, 2-methylbutan-1-ol, 2,2-dimethylpropan-1-ol, pentan-3-ol, pentan-2-ol, 3-methylbutan-2-ol, 2-methylbutan-2-ol. More preferably, the alcohol may be selected from C2-C4 alkyl substituted by one hydroxyl group or mixture thereof with the proviso that the alcohols contained in the mixture have the same number of carbon atoms. Advantageously, the invention is of interest for 1-butanol, 2-butanol, isobutanol or mixture thereof with the proviso that the mixture contains alcohols having the same number of carbon atoms. In particular, a mixture of butanol is used, preferably isobutanol is used.

The dehydration reactor can be a fixed bed reactor (radial, isothermal, adiabatic etc), a moving bed reactor, multitubular or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using several reactors in series of equal or different sizes or a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As preferred embodiment, the process for dehydration of a mono-alcohol or of a mixture of at least two mono-alcohols may be performed at a pressure ranging from 0.5 to 30 bars absolute (50 kPa to 3 MPa), advantageously from 0.5 to 15 bars absolute (50 kPa to 1.5 MPa), advantageously from 0.5 to 10 bars absolute (50 kPa to 1 MPa). Advantageously, the partial pressure of the alcohol is lower than 5 bars absolute (0.5 MPa) and more advantageously from 0.5 to 9 bars absolute (0.05 MPa to 0.9 MPa), preferably lower than 8 bars absolute (0.8 MPa) and more preferably lower than 7 bars absolute (0.7 MPa).

As preferred embodiment, the process for dehydration of a mono-alcohol or of a mixture of at least two mono-alcohols may be performed at a temperature ranging from 200° C. to 500° C., more advantageously from 225° C. to 450° C. and preferably from 250° C. to 400° C. These reaction temperatures refer mainly to the inlet temperature. Dehydration is an endothermic reaction and requires the input of reaction heat in order to maintain catalyst activity sufficiently high and shift the thermodynamic equilibrium to sufficiently high conversion levels. In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst back mixing the temperature in the catalyst bed approaches homogeneous conditions (a lot of back mixing) or approaches plug flow conditions (nearly no back mixing) and hence a decreasing temperature profile will install as the conversion proceeds. In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with inter heating of the reactor effluent from the first bed to higher temperatures and introducing the heated effluent in a second catalyst bed, etc. When fixed bed reactors are used, a multitubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As preferred embodiment, the process for dehydration of a mono-alcohol or of a mixture of at least two mono-alcohols may be performed with a weight hour space velocity ranging from 0.1 h−1 to 20 h−1, preferably from 0.5 h−1 to 10 h−1, more preferably from 1 h−1 to 9 h−1. The WHSV represents the weight flow rate of the mono-alcohol at the inlet of the reactor divided by the mass of the catalyst in said reactor.

The effluent of the process for the simultaneous dehydration and skeletal isomerization comprises essentially water, olefin, an inert component (if any) and unconverted mono-alcohol. Said unconverted mono-alcohol is supposed to be as low as possible. The olefin is recovered by usual fractionation means. Advantageously, the inert component, if any, is recycled in the feed (A) as well as the unconverted alcohol, if any.

The inert components, if any, is any component provided that there is no adverse effect on the catalyst comprising the modified crystalline aluminosilicate. Dehydration of a mono-alcohol is an endothermic reaction; the inert component can be used to bring energy to the reactor. For instance, the inert components can be selected among water, saturated hydrocarbons having up to 10 carbon atoms, naphthenes, nitrogen and $CO_2$. An example of inert components can be any individual saturated compound, a synthetic mixture of individual saturated compounds as well as some equilibrated refinery streams like straight naphtha, butanes etc. Advantageously, it is a saturated hydrocarbon or a mixture of saturated hydrocarbons having from 3 to 7 carbon atoms, more advantageously having from 4 to 6 carbon atoms and preferably pentane. The weight proportions of respectively alcohols, water and inert component are, for instance, 5-100/0-95/0-95 the total being 100.

In a preferred embodiment, said process for dehydration of a mono-alcohol or of a mixture of at least two mono-alcohols may further comprises a step of recovering and regenerating the catalyst.

In a preferred embodiment, at least 80% wt of the olefins obtained in said process for dehydration of a mono-alcohol have the same number of carbon atoms as the mono-alcohol, preferably at least 85% wt, more preferably at least 90% wt, in particular at least 95% wt.

In a preferred embodiment, the present process for dehydrating is carried out with a mixture of butanol as mono-alcohol, preferably isobutanol, and the mixture of olefins produced comprises at least 80% wt of butene and isomers thereof, preferably at least 90%, more preferably at least 95% wt, most preferably at least 98% wt. In addition, the selectivity in n-butenes may be at least 65% wt based on the total amount of butene and isomers thereof contained in the mixture of olefins produced, preferably at least 70% wt.

In another aspect of the present invention, the mixture of olefins produced by the process for dehydration of a mono-alcohol may be used as starting material for subsequent reactions such as the production of propylene via metathesis process, the production of butadiene via dehydrogenation, oligomerization, as well as for the production of transportation fuels, monomers and fuel additives. The mixture of olefins produced according to the present process may also replace the use of raffinate as defined in U.S. Pat. No. 4,282,389 in the refinery or petrochemical plants. The most typical application of a mixture containing isobutene is the conversion of the said isobutene into ethers (MTBE and ETBE), into t-butylalcohol (TBA) or oligomers (e.g. di/tri-iso-butenes), all being gasoline components. The higher oligomers of isobutene can be used for jet fuel applications. High purity isobutene can further be made by the decomposition of ethers (backcracking) or TBA (dehydration). High purity isobutene finds applications in the production of butyl-rubber, poly-isobutene, methylmethacrylate, isoprene, hydrocarbons resins, t-butyl-amine, alkyl-phenols and t-butyl-mercaptan. When the mixture of olefins contains n-butenes which have not reacted during the production of ethers or TBA and substantially not or only to a limited extent during the oligomerisation, said n-butenes have applications in the production of sec-butanol, alkylate (addition of isobutane to butenes), polygasoline, oxo-alcohols and propylene (metathesis with ethylene or self-metathesis between but-1-ene and but-2-ene). By means of super fractionation or extractive distillation or absorptive separation but-1-ene can be isolated from the n-butenes mixture. But-1-ene is used as comonomer for the production of polyethylenes, for polybut-1-ene and n-butyl-mercaptan. This involves an isomerization catalyst that is located in the distillation column and continuously converts the but-1-ene into but-2-ene, being a heavier component than but-1-ene. Doing so, a bottom product rich in but-2-ene and a top product poor in but-1-ene and rich in isobutene is produced. The bottom product can be used as described above. One main application of such but-2-ene rich stream is the metathesis with ethylene in order to produce propylene. If high purity iso-butene is desired the top product can be further super fractionated into substantially pure iso-butene and pure but-1-ene or the isobutene can be isolated via formation of ethers or TBA that is subsequently decomposed into pure iso-butene. The n-butenes rich stream may be used for the production of butadiene via dehydrogenation or oxidative dehydrogenation or send to alkylation unit to produce bio-alkylate. The mixture of isobutene and butenes can be sent to a catalytic cracking which is selective towards light olefins in the effluent, the process comprising contacting said isobutene and butenes mixture with an appropriate catalyst to produce an effluent with an olefin content of lower molecular weight than that of the feedstock. Said cracking catalyst can be a silicalite (MFI or MEL type) or a P-ZSM5.

Analytical Methods

Measure of the acidity of the crystalline aluminosilicate or of the modified aluminosilicate can be performed by temperature desorption of ammonia. Method known in the art suitable to quantify the acidic sites can be used. For instance, the method described in the procedure ASTM D4824-13 can be used. The amount of ammonia then determined via this method in cubic centimeter per grams can then be easily converted into µmol/g.

Alternatively measure of the amount of acid sites can for instance be done by temperature-programmed desorption of ammonia according the following method. The temperature-programmed desorption of ammonia is performed in a Pyrex®™ cell containing about 0.4 g of sample in form of the fraction 35-45 mesh. The cell is placed in an oven of the AUTOCHEM II 2920 equipped with TCD detector and the following steps are carried out:

Activation:

this step is performed under a flow rate of dried (over molecular sieve e.g. 3 A or 4 A) He of 50 cm$^3$/min (<0.001% of water). The temperature is increased from room temperature to 600° C. with a rate of 10° C./min. The temperature is then maintained at 600° C. during 1 h. The temperature is then decreased to 100° C. with a rate of 10° C./min.

Saturation:

this step is performed at 100° C. During a first hour, the solid is put in contact with a flow of 30 cm$^3$/min of a dried (over molecular sieve e.g. 3 A or 4 A, <0.001 of water) mixture of 10 weight % of NH$_3$ diluted in He. Then, during the next 2 h, the solid is put in contact with a flow rate of 50 cm$^3$/min of dried (over molecular sieve e.g. 3 A or 4 A, <0.001% of water) He to remove the physisorbed NH$_3$.

Analysis:

this step is performed under a flow of 50 cm$^3$/min of dried (over molecular sieve e.g. 3 A or 4 A, <0.001% of water) He. The temperature is increased to 600° C. with a rate of 10° C./min. Once the temperature of 600° C. has been reached, it is maintained for 1 h. The cell is then cooled down and weighted.

Calculation:

The amount of NH$_3$ desorbed from the solid is referenced to the weight of the sample by integrating the surface below the TCD curve and reporting to a calibration curve. The amount of NH$_3$ desorbed from the solid gives the acidity of the solid in µmol/g.

Measure of the content of transition metals and determination of the Si/Al framework molar ratio in the catalyst, in the modified crystalline aluminosilicate or in the crystalline aluminosilicate can be done by any suitable technique known in the art. For instance, it can be done using the method ASTM UOP961-12.

Alternatively measure of the Si/Al framework molar ratio in the catalyst, in the modified crystalline aluminosilicate or in the crystalline aluminosilicate can be determined using solid-state $^{29}$Si MAS NMR. All solid state $^{29}$Si MAS MAS NMR spectra were recorded on a Bruker DRX500 spectrometer (Pulse 45°, Relaxation delay 7 sec, rotor 4 mm). For a low defect zeolite samples, an aluminium atom will always be surrounded by four Silicones. The $^{29}$Si MAS NMR spectra of aluminosilicate zeolites give typically a series of peaks which correspond to SiO$_4$ tetrahedra in five different possible environments corresponding to different numbers of AlO$_4$ tetrahedra connected to the silicon via oxygen. For simplicity, these sites will be denoted ignoring the oxygen atoms as Si (4-nAl), where n is a number of Si in the tetrahedral: Si(0Al), Si(1Al), Si(2Al), Si(3Al), Si(4Al). The intensity of a silicon resonance is proportional to the number of associated silicon atoms. The number of Al atoms is proportional to a sum of the each corresponding peak multiplied by a number of Al (4-n) and divide by 4. The intensity of each resonance is determined by deconvolution: Si(0Al), Si(1Al), Si(2Al), Si(3Al), Si(4Al).

The Si/Al ratio is then given by the following equation:

Si/Al=4*Si total area/[Area Si(1Al)+2*Area Si(2Al)+3*Area Si(3Al)+4*Area Si(4Al)]

EXAMPLES

The Si/Al framework molar ratio was determined using solid-state $^{29}$Si MAS NMR measurement method described above.

The acidity was measured using the temperature-programmed desorption of ammonia method as described in the analytical methods above.

General procedure for dehydration process of alcohols is done as follows: A stainless-steel reactor tube having an internal diameter of 10 mm is used. 10 ml of the catalyst composition, as pellets of 35-45 mesh, is loaded in the tubular reactor. The void spaces, before and after the catalyst composition, are filled with SiC granulates of 2 mm. The temperature profile is monitored with the aid of a thermocouple well placed inside the reactor at the top of the catalyst bed. Before the reaction, the catalyst was pretreated in a nitrogen flow at 550° C. for 2 h (heating rate 60° C./h) followed by cooling down to the reaction temperature. The nitrogen is then replaced by the feed at the indicated operating conditions. The catalytic tests are performed down-flow, in a pressure range from 1.5 to 11 bars, in a temperature range of 100–500° C. and with an alcohol weight hour space velocity varying from 0.1-20 h$^{-1}$ (kg of product/hours×kg of catalyst). Analysis of the products is performed by using an on-line gas chromatography.

Example 1

Sample A is made of FER55 (CP914 from Zeolyst international), extruded with SiO$_2$ (FER/SiO$_2$: 70/30). It is characterized by having a Si/Al in the zeolite framework of 28 and an acidity of 750 μmol/g.

Example 2

Sample B has been obtained by steaming sample A with deionized water at 300° C. at 8.8 bars during 24 h hours with a weight hour speed velocity (whsv) of 7.9 h−1 and under an atmosphere containing 100% of steam (i.e. at a partial pressure of H$_2$O of 8.8 bars). Sample B is characterized by having an acidity of 500 μmol/g.

Example 3

Sample C has been obtained by steaming sample A with deionized water at 300° C. at 8.8 bars during 6 days with a weight hour speed velocity (whsv) of 7.9 h−1 and under an atmosphere containing 100% of steam (i.e. at a partial pressure of H$_2$O of 8.8 bars). Sample C is characterized by having an acidity of 400 μmol/g.

Example 4

Sample D has been obtained by steaming sample A with deionized water at 350° C. at 8.8 bars during 24 hours with a weight hour speed velocity (whsv) of 7.9 h−1 and under an atmosphere containing 100% of steam (i.e. at a partial pressure of H$_2$O of 8.8 bars). Sample C is characterized by having an acidity of 425 μmol/g.

Example 5

Sample E has been obtained by steaming sample A according to a standard procedure: steaming with deionized water at 600° C. under atmospheric pressure during 6 hours with a weight hour speed velocity (whsv) of 0.5 h−1 and under an atmosphere containing 100% of steam. Sample E is characterized by having an acidity of 300 μmol/g.

Example 6

Sample F has been obtained by steaming sample A according to a standard procedure: steaming with deionized water at 300° C. under atmospheric pressure during 24 hours with a weight hour speed velocity (whsv) of 7.9 h−1 and under an atmosphere containing 100% of steam. Sample F is characterized by having an acidity of 550 μmol/g.

Example 7 (Comparison)

The catalysts described in the examples 1 to 5 have been crushed and sieved (35-45 mesh) for loading 10 mL in a fixed bed reactor. The catalysts are then subjected to isobutanol dehydration testing. The testing conditions are a pressure of 3 bars, a temperature between 250 and 350° C. (isothermal) and an isobutanol weight hour space velocity (WHSV) of 7 h−1. Isobutanol was diluted with H2O, the ratio iBuOH/H2O=95/5. The results obtained at 300° C. and 350° C. are presented in Table 1.

TABLE 1

Isobutanol dehydration test results under isothermal conditions.

| | Reaction Temp.: 300° C. | | | Reaction Temp.: 350° C. | | |
|---|---|---|---|---|---|---|
| | iBuOH conv. | C4 = sel. | nC4 = sel. | iBuOH conv. | C4 = sel. | nC4 = sel. |
| Sample A (base) | 100% | 97.5% | 80.5% | 100% | 97.0% | 73.0% |
| Sample B (invention) | 100% | 98.5% | 82.0% | 100% | 97.5% | 77.0% |
| Sample C (invention) | 100% | 99.0% | 83.5% | 100% | 98.5% | 80.5% |
| Sample D (invention) | 100% | 99.0% | 86.0% | 100% | 99.0% | 80.0% |
| Sample E (comparative) | 87.0% | 99.0% | 75.0% | 100% | 98.0% | 65.5% |
| Sample F (comparative) | 100% | 97.0% | 80.5% | 100% | 97.0% | 65.5% |

At a reaction temperature of 300° C. (Table 1), the catalysts treated according the present invention have similar isobutanol conversion but improved selectivity towards linear butenes compared to base catalyst (Sample A). The comparative sample E has lower conversion and lower selectivity while comparative sample F is similar to base catalyst (Sample A)

At a reaction temperature of 350° C. (Table 1), the catalysts treated according the present invention have similar isobutanol conversion but improved selectivity towards linear butenes compared to base catalyst (Sample A) while the comparative samples E and F are much less selective.

Example 8 (Comparison)

Sample A and sample B have been tested under adiabatic condition. The testing conditions are a pressure of 8.8 bars, an entrance temperature of 350° C. (adiabatic) and an isobutanol weight hour space velocity (WHSV) of 7 h−1. For this test, 200 mL of extruded catalysts which were blended with 200 ml of SiC are placed in 2 reactors (100 ml of catalyst per reactor). The reactors were installed in a series with an intermediate reheating. The results obtained after 100 h on stream are presented in Table 2.

TABLE 2

Isobutanol dehydration test results under adiabatic conditions.

| | iBuOH conv. | C4 = sel. | nC4 = sel. |
|---|---|---|---|
| Sample A (base) | 99.5% | 99.0% | 78.0% |
| Sample B (invention) | 99.5% | 99.0% | 83.5% |

According to testing results under adiabatic conditions (Table 2), the catalysts treated according to the present invention have similar isobutanol conversion but improved selectivity towards linear butenes compared to base catalyst (Sample A).

Example 9 (Comparison)

Samples A, B and D have been loaded, in a 3 parallel fixed beds reactors (316L stainless steel, 13 mm internal diameter, downflow operating). 1.5 g of extruded catalysts are diluted with 200 μm SiC. The catalyst is activated under air (6NL/h) at 450° C. (10° C./min) during 1 h. The catalysts are then subjected to isobutanol dehydration testing under these conditions: a pressure of 8.8 bars, a temperature of 300° C.

(isothermal) and an isobutanol weight hour space velocity (WHSV) of 7 h−1. Isobutanol was diluted with H2O, the ratio iBuOH/H2O=95/5 w/w. The results obtained in these conditions, after 50 h and after 300 h on stream, are presented here below (Table 3).

TABLE 3

Isobutanol dehydration test results under isothermal conditions (300° C.) at different time on stream.

|  | Time on stream: 50 h | | | Time on stream: 300 h | | |
| --- | --- | --- | --- | --- | --- | --- |
|  | iBuOH conv. | C4 = sel. | nC4 = sel. | iBuOH conv. | C4 = sel. | nC4 = sel. |
| Sample A (base) | 100% | 98.5% | 83.5% | 87.0% | 99.5% | 84.0% |
| Sample B (invention) | 100% | 99.0% | 85.0% | 99.0% | 99.5% | 85.0% |
| Sample D (invention) | 100% | 99.0% | 85.0% | 99.0% | 99.5% | 85.0% |

At a reaction temperature of 300° C., after 50 h on stream (Table 3, left part), the catalysts treated according the present invention have similar isobutanol conversion but improved selectivity towards linear butenes compared to base catalyst (Sample A). At longer reaction time, at 300° C. (Table 3, right part), the isobutanol conversion obtained with base catalyst (Sample A) drops while samples prepared according to the invention maintain high conversion. Furthermore, the catalysts treated according the present invention retain better selectivity towards linear butenes and better stability compared to base catalyst (Sample A).

As shown in the present examples, the catalysts according to the present invention have several advantages compared to the catalysts known in the art.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The invention claimed is:

1. A process for dehydration of a mono-alcohol, or of a mixture of at least two mono-alcohols, having at least 2 carbon atoms and at most 7 carbon atoms into olefins having the same number of carbons, the process comprising the following steps:
   i.) providing a catalyst composition;
   ii.) providing a feed (A) comprising said mono-alcohol, or said mixture of at least two mono-alcohols, optionally water, and optionally an inert component;
   iii.) contacting said feed (A) with said catalyst at conditions effective to dehydrate at least a portion of said mono-alcohol and;
   iv.) recovering an effluent (B) and removing water, the inert component if any and unconverted alcohols if any from said effluent (B) to recover said olefins having the same number of carbons as said mono-alcohol;
characterized in that said catalyst composition comprises a modified crystalline aluminosilicate having an acidity between 350 and 500 μmol/g measured by temperature programmed desorption of ammonia, wherein said process further comprises a process for preparing said catalyst composition comprising the following steps:
   a) providing a crystalline aluminosilicate having a Si/Al framework molar ratio greater than 10;
   b) optionally shaping and/or calcining said crystalline aluminosilicate;
   c) steaming said crystalline aluminosilicate, or said shaped and/or calcined crystalline aluminosilicate:
      at a temperature ranging from 100° C. to 380° C.;
      under a gas phase atmosphere, without liquid, containing from 5 wt % to 100 wt % of steam and the rest being one or more gases selected from $N_2$, $CO_2$, Ar, He, $CH_4$, air, depleted air containing below 10 wt % of oxygen as based on the total weight of the depleted air, or any mixture thereof;
      at a pressure ranging from 2 to 200 bars;
      at a partial pressure of $H_2O$ from 2 bars to 200 bars; and
      said steaming being performed for a period at least 30 min and up to 144 h.

2. The process for dehydration of a mono-alcohol, or of a mixture of at least two mono-alcohols, according to claim 1, characterized in that the step c) of steaming said crystalline aluminosilicate is performed:
   at a temperature of at least 200° C.; and/or
   a temperature of at most 350° C.; and/or
   at a pressure ranging from 2 to 20 bars; and/or
   at a partial pressure of $H_2O$ from 3 to 10 bars.

3. The process for dehydration of a mono-alcohol, or of a mixture of at least two mono-alcohols, according to claim 1, characterized in that said process for preparing said catalyst composition further comprises the following steps:
   not performing any leaching treatment either before step b) or after step c) in order to maintain constant the concentration of aluminium in the modified crystalline aluminosilicate;
   performing an optional step of washing or ion exchange with an alkali metal or $NH_4$ salts after step c) or before step b);
   performing an optional calcination step of the product obtained after step c) or before step b); and/or
   performing an optional step of recovering said modified crystalline aluminosilicate after c).

4. The process for dehydration of a mono-alcohol, or of a mixture of at least two mono-alcohols, according to claim 1, characterized in that said crystalline aluminosilicate is a 10 membered ring zeolite of the Framework Type FER, MWW, EUO, MFS, ZSM-48, MTT, MFI, MEL, TON or SZR and is chosen among ferrierite, FU-9, ISI-6, NU-23, Sr-D, ZSM-35, ZSM-57 or SUZ-4 or any mixture thereof.

5. The process for dehydration of a mono-alcohol, or of a mixture of at least two mono-alcohols, according to claim 1, characterized in that said crystalline aluminosilicate is shaped or extruded prior to any of steps a) to c) with a binder selected from $AlPO_4$, clay, zirconia, titania oxide or silica.

6. The process for dehydration of a mono-alcohol, or of a mixture of at least two mono-alcohols, according to claim 5, characterized in that said steaming of step c) is performed on a shaped or extruded crystalline aluminosilicate in situ prior to step iii.) of said process for dehydration of a mono-alcohol to obtain said catalyst.

7. The process for dehydration of a mono-alcohol, or of a mixture of at least two mono-alcohols, according to claim 1, wherein the product obtained after step c) is further shaped or extruded with a binder selected from $AlPO_4$, clay, zirconia, titania oxide or silica.

8. The process for dehydration of a mono-alcohol, or of a mixture of at least two mono-alcohols, according to claim 5, characterized in that the binder is selected to comprise:
- at least 85 wt % of silica as based on the total weight of the binder; and/or
- less than 1000 ppm by weight as based on the total weight of the binder of aluminium, gallium, boron, iron and/or chromium.

9. The process for dehydration of a mono-alcohol, or of a mixture of at least two mono-alcohols, according to claim 1, wherein neither any steaming at a temperature higher than 380° C. nor any leaching has been performed on said crystalline aluminosilicate prior to step a) and wherein neither any steaming at a temperature higher than 380° C. nor any leaching is further performed on said modified aluminosilicate after step c).

10. The process for dehydration of a mono-alcohol, or of a mixture of at least two mono-alcohols, according to claim 1, characterized in that said modified crystalline aluminosilicate has an acidity between 350 and 450 µmol/g measured by temperature programmed desorption of ammonia.

11. The process for dehydration of a mono-alcohol, or of a mixture of at least two mono-alcohols, according to claim 1, characterized in that said modified crystalline aluminosilicate has Si/Al framework molar ratio ranging from 10 to 65.

12. The process for dehydration of a mono-alcohol, or of a mixture of at least two mono-alcohols, according to claim 1, characterized in that said modified crystalline aluminosilicate has a content of transition metals or cations thereof lower than 1000 wt ppm measured by the method ASTM UOP961-12, said transition metals belonging to any of the columns 3 to 12 of the Periodic Table.

13. The process for dehydration of a mono-alcohol, or of a mixture of at least two mono-alcohols, according to claim 1, characterized in that said conditions effective to dehydrate said mono-alcohol into said olefins having the same number of carbons are any combinations of:
- adiabatic or isotherm operating conditions or any of intermediate conditions in between including partial heat compensation or intermediate re-heating; and/or
- a temperature ranging from 200° C. to 500° C.; and/or
- a pressure ranging from 0.5 bar to 15 bars (50 kPa to 1.5 MPa); and/or
- a WHSV ranging from 1 to 30 $h^{-1}$ wherein the WHSV represents the weight flow rate of said mono-alcohol at the inlet of the reactor divided by the mass of the catalyst composition in said reactor; and/or
- said feed (A) having a partial pressure of alcohols from 0.1 to 15 bars absolute (0.01 MPa to 1.5 MPa).

14. The process for dehydration of a mono-alcohol, or of a mixture of at least two mono-alcohols, according to claim 1, characterized in that said mono-alcohol(s) has at least 4 carbon atoms and in that said dehydration of a mono-alcohol is performed together with a skeletal isomerization.

15. The process for dehydration of a mono-alcohol, or of a mixture of at least two mono-alcohols, according to claim 14, characterized in that said mono-alcohol is isobutanol and in that said isobutanol is converted into n-butenes and isobutene.

* * * * *